United States Patent [19]

Lowne

[11] Patent Number: 4,552,458
[45] Date of Patent: Nov. 12, 1985

[54] COMPACT REFLECTOMETER

[75] Inventor: Alan J. Lowne, Rochester, N.Y.

[73] Assignee: Eastman Kodak Company, Rochester, N.Y.

[21] Appl. No.: 540,729

[22] Filed: Oct. 11, 1983

[51] Int. Cl.$^4$ .................................................. G01N 21/47
[52] U.S. Cl. ........................................ 356/446; 422/55
[58] Field of Search ................... 356/445, 446, 39, 42, 356/38, 71, 73, 447, 448; 422/68, 57, 55; 250/559

[56] References Cited

U.S. PATENT DOCUMENTS

| | | | |
|---|---|---|---|
| 2,451,501 | 10/1948 | Liben | 356/445 |
| 3,910,701 | 10/1975 | Henderson et al. | 356/73 X |
| 3,986,778 | 10/1976 | Mathisen et al. | 356/244 |
| 4,097,743 | 6/1978 | Carlson | 250/339 |
| 4,147,430 | 4/1979 | Gorgone et al. | 356/71 X |
| 4,153,369 | 5/1979 | Kallet et al. | 356/318 |
| 4,246,489 | 1/1981 | Yoshida et al. | 250/577 |

FOREIGN PATENT DOCUMENTS

| | | | |
|---|---|---|---|
| 0071287 | 6/1977 | Japan | 356/448 |
| 56-47734 | 4/1981 | Japan | 356/437 |

OTHER PUBLICATIONS

"Applied Optics", Querry, vol. 17, pp. 3587-3592.
"Glucoscan" Owner's Manual.

Primary Examiner—Vincent P. McGraw
Assistant Examiner—Robert Thompson
Attorney, Agent, or Firm—Dana M. Schmidt

[57] ABSTRACT

A thin, compact reflectometer is adapted to support and position a generally planar test element in a predetermined, generally horizontal plane during usage. The reflectometer includes a light source and a detector having major portions of their respective illumination and detection axes extending generally parallel to a planar reflectometer-positioning portion on one of two major surfaces of the reflectometer.

8 Claims, 7 Drawing Figures

COMPACT REFLECTOMETER

FIELD OF THE INVENTION

This invention relates to a compact reflectometer, and particularly to one designed to be used as an analyzer carried by a patient.

BACKGROUND OF THE INVENTION

Recent emphasis has been placed upon compact reflectometers that can be used directly by the patient as a blood analyzer. Particularly such reflectometers are needed by diabetics who take repeated measurements of the glucose levels of their whole blood. Most properly, such reading should be taken at regular intervals, wherever the patient finds himself. This is not possible unless the reflectometer is readily portable. Portability requires more than just being lightweight or small—the bulk and shape also dictate whether the reflectometer is convenient to carry. A truly portable and convenient reflectometer would be one which would fit, for example, in the patient's shirt or coat pocket. Preferably, such a reflectometer should not be thicker than 2 cm.

Commonly owned, copending application Ser. No. 401,754 filed by J. W. Ward on July 26, 1982, and entitled "Light Guide Reflectometer" describes a reflectometer featuring a light guide one interior surface of which acts as a mirror to reflect light from a light source to the horizontally supported test element. Such mirrored surface allows the light source to be displaced at an angle to, that is, to one side of, the normal to the test element, thereby permitting some reduction in thickness. However, because the conventional approach has been to "read" the element by detecting radiation diffusely reflected at 90° from the test element, the detector of necessity was placed under the test element. That is, it is conventional to direct incoming light at an angle of 45° to the test element, and to detect diffusely reflected light at an angle of 90° thereto, i.e., normal to the plane. This angular arrangement eliminates detection of specular reflection, namely that which is reflected at 45°. However, such an optical arrangement dictates the placement of the photodetector directly opposite to the supported test element. Although commercially available inexpensive detectors now have a reduced thickness, they still have an appreciable thickness that adds to the thickness of the photometer if the detectors are placed under the examined test element. The added thickness detracts from portability.

However, portability is not the only requirement. The reflectometer must be one that is otherwise convenient to use, to insure that it will be used as often as is required. Pocket-sized reflectometers have been provided with convenient thicknesses by constructing the axes of the light source and detector to be generally parallel to the planes of the major exterior surfaces (see for example, those described in the owner's Manual of the "Glucoscan" analyzer, published in 1982 by Lifescan). However, those reflectometers feature a test element that is oriented vertically when the reflectometer is placed in its normal resting position. Such vertical orientation has disadvantages, since any excess blood or serum sample on the absorbing pad of the test element will run off into the reflectometer and provide possible contamination. As a result, the patient must either blot off the excess, or wait until it is fully absorbed. In either case, the patient experiences an inconvenience. Also reflectometers such as the "Glucoscan" described above require the test element to be properly aligned with a thin, small slot in order to insert the pad into the reflectometer. This can be a difficulty for elderly or infirm patients.

Thus there has been a need, prior to this invention, for a compact reflectometer that is adapted to read a test element supported in a generally horizontal orientation, and particularly one that so supports the element on a readily accessible support surface.

SUMMARY OF THE INVENTION

I have discovered that, unlike the above-noted prior reflectometers, the test element can be supported horizontally by the reflectometer during use, and still feature a thickness appropriate to fitting the reflectometer in a pocket. The thickness is minimized by orienting the light source and the detector so that their respective illuminating and detecting axes are each generally parallel to a planar reflectometer-positioning portion on one of the two major surfaces of the reflectometer.

More specifically, there is provided a compact reflectometer comprising wall means providing two major exterior surfaces which are generally planar and parallel, means for supporting a generally planar test element in a predetermined plane of the reflectometer, planar means on one of the major surfaces for positioning the reflectometer on a rest surface during use so that the predetermined support plane is generally horizontal, a light source constructed to project a beam of light centered on an axis of illumination, and light detector means constructed to receive light centered on an axis of detection. The light source and the detector means are disposed with their axes each being generally parallel to the planar positioning means of one of the major surfaces. The reflectometer further includes directing means for directing (a) light from the source to the predetermined plane, and (b) diffusely reflected light from the predetermined plane to the detector means.

In a preferred embodiment of the invention, the aforesaid predetermined plane of support of the test element is also generally parallel to the axes of the light source and the detector means, and the directing means includes a reflecting surface.

Thus, it is an advantage of the present invention that the reflectometer accepts a horizontally-positioned test element on a readily-accessible surface, and can have a thickness no greater than 2 cm.

It is a related advantage of the invention that a pocket-sized reflectometer is provided for use as an analyzer, wherein the risk of contamination of the instrument by the patient's sample is substantially reduced.

It is another advantage of the invention that such a reflectometer can include a second detector means to function as a reference that is used to control and maintain constant the output of the light source, without sacrificing thinness.

It is yet another advantage of the invention that such a reflectometer can include a second light source for illuminating the test element at a different wavelength, without sacrificing thinness.

Other features and advantages will become apparent upon reference to the following Description of the Preferred Embodiments, when read in light of the attached drawings.

DESCRIPTION OF THE PREFERRED EMBODIMENTS

The invention is hereinafter described particularly with respect to the preferred embodiments wherein the reflectometer of the invention is used as an analyzer of whole blood. The invention further is described in the preferred context of analyzing whole blood for glucose. In addition, the invention is useful in analyzing other biological liquids besides whole blood, and for analytes other than glucose. It is further useful as a reflectometer having a use other than as an analyzer, particularly where there is a need for compactness similar to that in clinical analysis.

As used herein, "biological liquids" means all liquids obtained from animals, including whole blood, plasma, serum, sweat, spinal fluid and urine, and liquids compatible with these animal liquids, such as control fluids, saline solutions and diluents.

Figure 1:
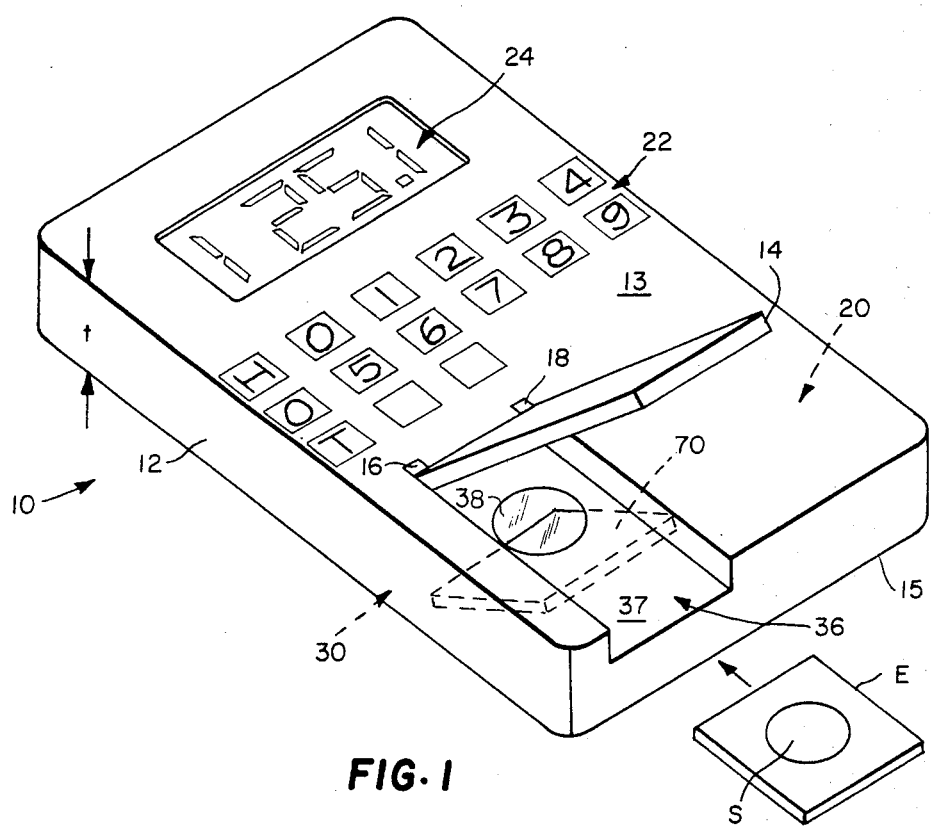
FIG. 1 is an isometric view of a reflectometer constructed in accordance with the invention.
Figure 2:
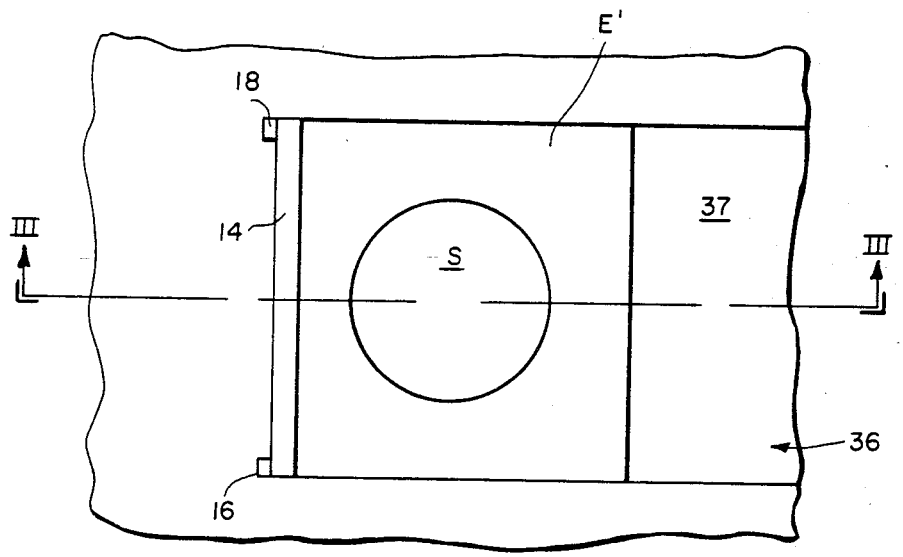
FIG. 2 is a fragmentary plan view of a test element on the supporting surface of the reflectometer.

FIG. 1 illustrates a reflectometer 10 constructed in accordance with the invention. A housing 12, which can be in one or several pieces, encases optic portions 30 discussed in detail hereinafter. The housing features two major exterior surfaces which have major portions 13 and 15, respectively, that are generally planar. Most preferably, portions 13 and 15 are also generally parallel. As used herein, the recitation of a feature of the reflectometer being "generally parallel" to a surface or plane, means being no more than 10° inclined to that surface or plane. "Major exterior surface" herein refers to the largest exterior surface.

A cover 14 for the reflectometer is pivotally attached at 16 and 18 to the housing by conventional means. Also included are a microcomputer 20, and input/output devices comprising a keyboard 22 and a display 24, respectively.

Reflectometer 10 is intended to function with generally planar test elements E that contain all the necessary reagents in dried form in one or more layers, of which layer S is adapted to receive a patient sample. The test elements E and E' are only schematically illustrated in the drawings. Useful test elements are generally described in U.S. Pat. Nos. 3,992,158 issued on Nov. 16, 1976 and 4,258,001 issued on Mar. 24, 1981. Test elements of this type are currently available under the trademark "Ektachem" from Eastman Kodak Company, Rochester, N.Y. If the analyzer is particularly used to assay for whole blood glucose, a preferred test element is the type described in commonly owned U.S. application Ser. No. 444,112 filed on Nov. 24, 1982 by R. Gross et al entitled "Analytical Element Containing a Barrier Zone and Process Employing Same."

More particularly, such a whole blood glucose test element preferably comprises, in sequence, a support zone, a reagent zone, a barrier zone, and a porous spreading zone. The most preferred form of such a test element is one in which the zones are in layers, and the barrier layer is a non-porous film comprising a polymer of which from 30 to 95 percent by weight is polymerized from a monomer having the structure

from 0.25 to 30% by weight is polymerized from a monomer having the structure

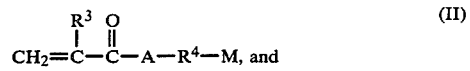

from 0.1 to 50% by weight is polymerized from a monomer having the structure

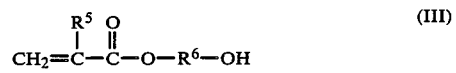

where $R^1$, $R^3$, and $R^5$ are independently selected from the group consisting of hydrogen and methyl;

$R^2$ is alkyl of from 1 to 16 carbon atoms;

$R^4$ and $R^6$ are independently selected from the group consisting of alkylene groups having from 1 to 6 carbon atoms;

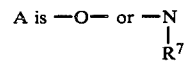

where $R^7$ is hydrogen, alkyl of 1 to 10 carbon atoms, or cycloalkyl of 5 to 10 carbon atoms, and M is $NR^8R^9H^\oplus X$ or $SO_3X$, where $R^8$ and $R^9$ are independently selected from the group consisting of hydrogen and alkyl of 1 to 4 carbon atoms, and X is a counterion. Such polymers are in the form of an amine salt or a sulfonate salt. In the case of the amine salt, it is preferred that the salt be the hydrohalide, especially the hydrochloride. Where the polymerized monomer contains a sulfonate group, it will generally be convenient for it to be in the form of an alkali metal salt, such as $Na^\oplus$ or $K^\oplus$, although other salts can be used as long as the monomer retains water solubility. Thus, X can be a positively charged ion such as $Na^\oplus$, $K^\oplus$, or $H^\oplus$ or a negatively charged ion such as chloride, sulfonate, or the like.

Preferred polymers of the barrier zone of the improved elements for whole blood glucose analysis are synthesized from the following monomers: n-butyl methacrylate, 2-methacryloyloxyethyl-1-sulfonic acid, sodium salt, 2-acetoacetoxyethyl methacrylate, 2-hydroxyethyl methacrylate, 2-aminoethyl methacrylate hydrochloride, and 2-ethylhexyl methacrylate. The preferred polymers include: poly(n-butyl methacrylate-co-2-methacryloyloxyethyl-1-sulfonic acid-co-2-acetoacetoxyethyl methacrylate-co-2-hydroxyethyl methacrylate) (60/5/10/25, 70/2.5/10/17.5, or 60/10/10/20); poly(2-ethylhexyl methacrylate-co-methacryloyloxyethyl-1-sulfonic acid-co-2-acetoacetoxyethyl methacrylate-co-2-hydroxyethyl methacrylate) (50/2.5/10/37.5); and poly(n-butyl methacrylate-co-2-aminoethyl methacrylate hydrochloride-co-2-hydroxyethyl methacrylate) (50/15/35); where the numbers in parentheses are weight percentages of the monomers in the polymerization mixture.

The polymerization is generally carried out at a temperature below about 100° C., in a solution in organic solvents, e.g. the lower alcohols, dimethyl sulfoxide, dimethylformamide, and the like, and then, if desired, the polymeric product is dispersed in water. Latex polymerization can also be employed although the barrier properties of the polymers prepared in this way have been inferior to those obtained using solution polymerization.

The concentration of total polymerizable monomer in the polymerization mixture can be varied widely with concentrations up to about 60 percent by weight and, preferably about 20 to about 40 percent by weight, based on the weight of the monomers, plus solvent, being satisfactory.

Suitable catalysts for the polymerization reaction include, for example, the free radical catalysts, such as hydrogen peroxide, cumene hydroperoxide, azo type initiators, and the like. In redox polymerization systems, conventional ingredients can be employed.

Any conventional microcomputer 20, FIG. 1, keyboard 22 or output display 24 is useful, although the miniaturized types are preferred. For example, a liquid crystal display 24 is preferred. These components are electrically connected in a conventional manner, FIG. 6, through a signal processing circuit 200 hereinafter discussed.

Figure 3:
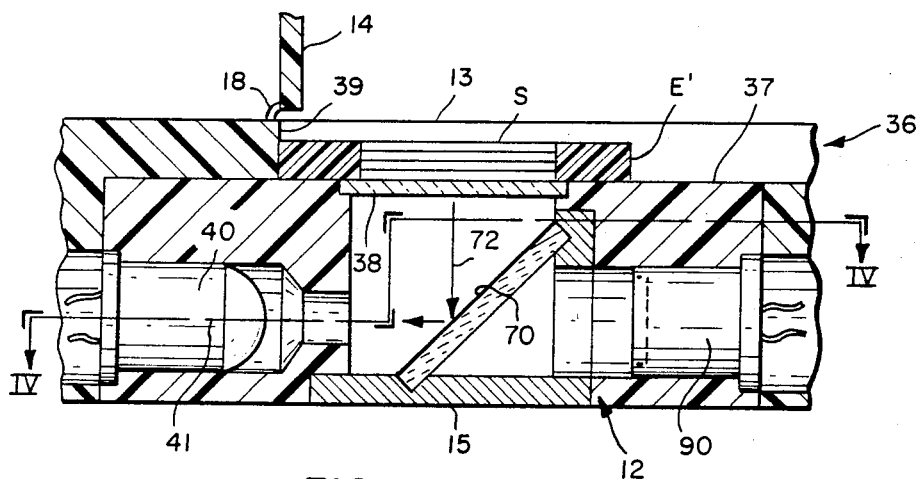
FIG. 3 is a fragmentary sectional view taken generally along the line III—III of FIG. 2.
Figure 4:
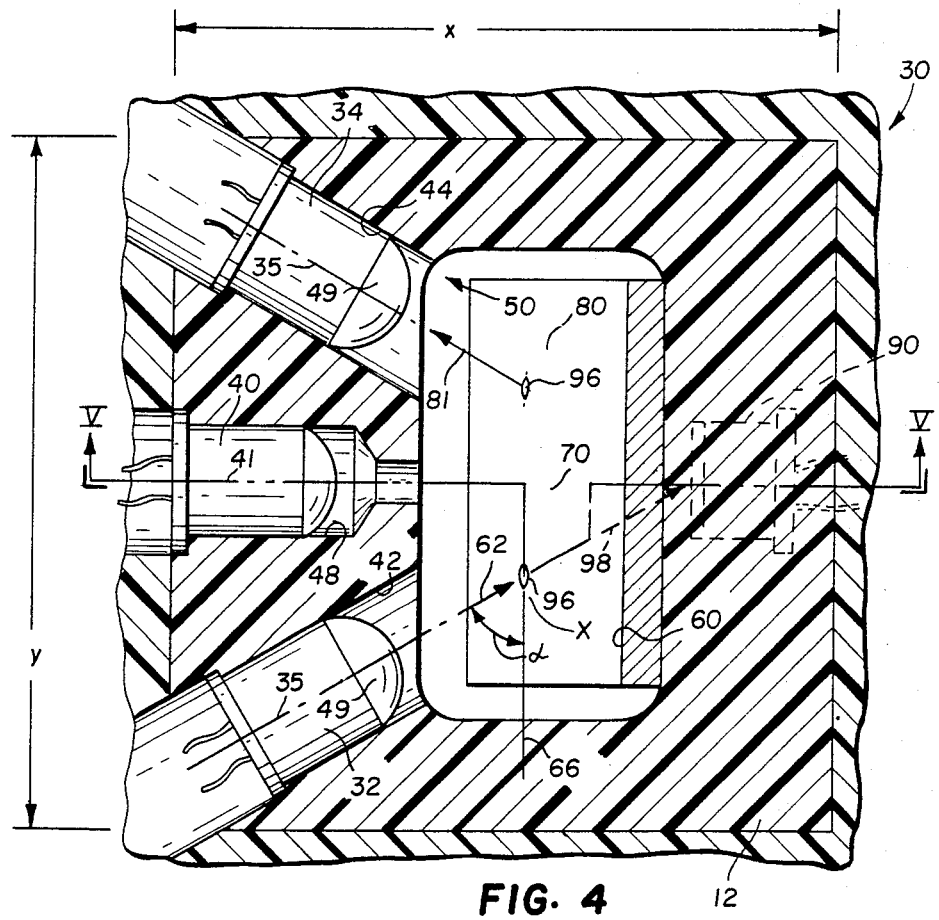
FIG. 4 is a fragmentary sectional view taken generally along the path IV—IV of FIG. 3.
Figure 5:
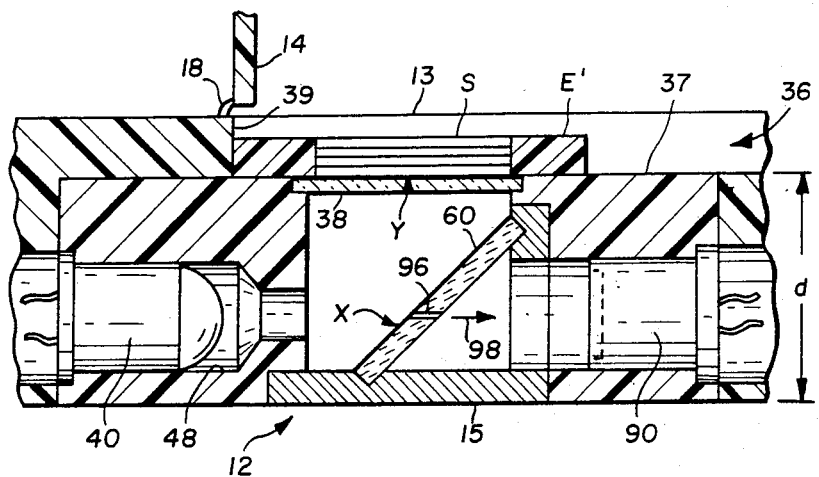
FIG. 5 is a fragmentary sectional view taken along the path V—V of FIG. 4.

The various optic portions 30 of one preferred reflectometer, are shown in FIGS. 1–5. This embodiment includes light sources 32 and 34 each emitting a light beam centered on an axis of illumination 35 (FIG. 4), a support groove 36 for supporting horizontally a test element E or E' (FIGS. 1 and 2), such groove including a preferably planar support surface 37, a glass plate 38 mounted within housing 12 to provide a window to the element, and a stop surface 39 (FIG. 3) for abutting the test elements. Plate 38 is also preferably planar. A detector 40 such as a photodiode (FIGS. 3 and 4) which detects light along a path that is centered on an axis of detection 41, is included to detect diffusely reflected radiation from a supported test element E'. Light source 34 (FIG. 4) is preferably identical to source 32, except that the two emit light radiation at two different wavelengths, for example, red and green. Each of the light sources 32, 34 and detector 40 are mounted in appropriately shaped pockets 42, 44 and 48, respectively, (FIG. 4), formed within housing 12 adjacent to bottom surface portion 15 of housing 12 (FIG. 5). Preferably, the axes of pockets 42 and 44 are angled at about 30° to the axis of pocket 48 (FIG. 4) while forming a common plane with each other and the axis of pocket 48. Most importantly, that common plane is generally parallel to major portion 13 of the major exterior surface. That plane most preferably is also generally parallel to plate 38 (FIG. 3) to insure the axes 35 and 41 of the light sources and detector are also generally parallel to the plane of the supported test element. Light sources 32 and 34 most preferably have lens 49 that tend to collimate the light into narrow beams centered on their respective axes 35.

Because of the aforedescribed construction wherein the axes of the light source and detector of the reflectometer are parallel to the supported test element, a major portion of the dimensions that are ordinarily required between the light source or detector, and the test element, extend sideways, parallel to the plane of the test element and to the major exterior planes of the reflectometer, rather than perpendicular to that plane. The thickness of the reflectometer is therefore minimized.

The reflectometer preferably also includes a light trap 50, FIG. 4, for receiving light specularly reflected from the test element. Most preferably, light trap 50 comprises the other light source 34. Similarly, light source 32 acts as a light trap when light source 34 is operative. However, any other light trap, such as a light-absorbing surface, is also useful.

Optic portions 30 include reflecting means, which most preferably is a reflecting surface 60, FIGS. 3–5, for reflecting illuminating radiation along path 62, FIG. 4, from light source 32 onto supported test element E'. Such radiation proceeds from source 32 to a spot, generally designated "X", on surface 60. Most of the radiation is reflected to a spot "Y" generally centered on a supported test element, FIG. 5. To so direct the light from light source 32 to the test element, reflecting surface 60 is mounted within housing 12 so as to form an angle of 45° to surface 37.

Any conventional mirrored or reflective surface 60 will suffice, it being preferred that the surface be generally planar. The 45° orientation noted above is achieved by rotating the surface about one of its axes 66, FIG. 4.

Optic portions 30 also include, FIGS. 3 and 4, a reflecting surface 70 for reflecting some of the diffusely reflected light from test element E', along folded path 72 to detector 40. Surface 70 is also disposed at an angle of 45° to the plane of surface 37.

It will be appreciated that reflecting surfaces 60 and 70 preferably fall in the same plane.

Because of such mirrored surfaces, illuminating radiation path 62 impinges at X onto surface 60 at angle alpha, FIG. 4, measured from axis 66. Path 62 is reflected up to and through plate 38 to the supported test element at an angle also equal to alpha. Light diffusely reflected from the test element at 90° (i.e., normal therefrom) is then reflected, FIG. 3, by surface 70 along folded path 72 to detector 40. Angle alpha is chosen to be as close to 90° as possible to maximize the light output of the diffuse reflection along path 72, without adding specular reflection to path 72. A particularly useful value for alpha is about 60°.

Most preferably, surfaces 60 and 70 comprise a single mirror. Preferably this same mirror provides a surface 80, FIG. 4, to reflect along path 81, specular reflectance from element E' to the light trap 50 formed by light source 34. Alternatively, surfaces 60, 70 and 80 can comprise three separate mirrors side-by-side.

Because a reflecting surface is used to fold the paths of both the illuminating light and the light diffusely reflected from test element E', both the light sources 32, 34 and the detector 40 can be disposed to one side, which is the left side as shown in FIG. 4, of the normal to the plane of element E'. As a result, distance "d", FIG. 5, namely the thickness of the reflectometer measured from support surface 37 to the major planar portion 15 of the bottom wall of housing 12, is minimized since that distance does not have to also include the added value of the thickness of the detector. Such distance is, in one example, no greater than 9 mm.

In accordance with another aspect of the invention, a second, reference detector 90 is disposed generally opposite to and coaxial with detector 40 to receive a small fraction (e.g., 10%) of the illuminating light that impinges on surface 60. As shown, surface 60 is apertured at 96 to allow such small fraction to pass through and towards detector 90 along path 98, FIGS. 4 and 5. To allow detector 90 to also receive a portion of the illuminating radiation from light source 34 in a similar manner, FIG. 4, detector 90 is a wide-angle detector such as PIN photodiode VTB 5051 obtainable from VACTEC. Detector 40, for example is a photodiode VTB 1113 obtainable also from VACTEC.

Alternatively, surfaces 60 and 80 are only partially silvered at 96, to allow 10% of the illuminating radiation to be transmitted through to detector 90.

As will be readily apparent, light sources 32 and 34 are preferably LED's because of their size. Useful examples include those available from So Li Co., for example a red LED having the designation ESBR/SBR 5501, and a green LED having the designation ESBG/SBG 5501.

Figure 6:
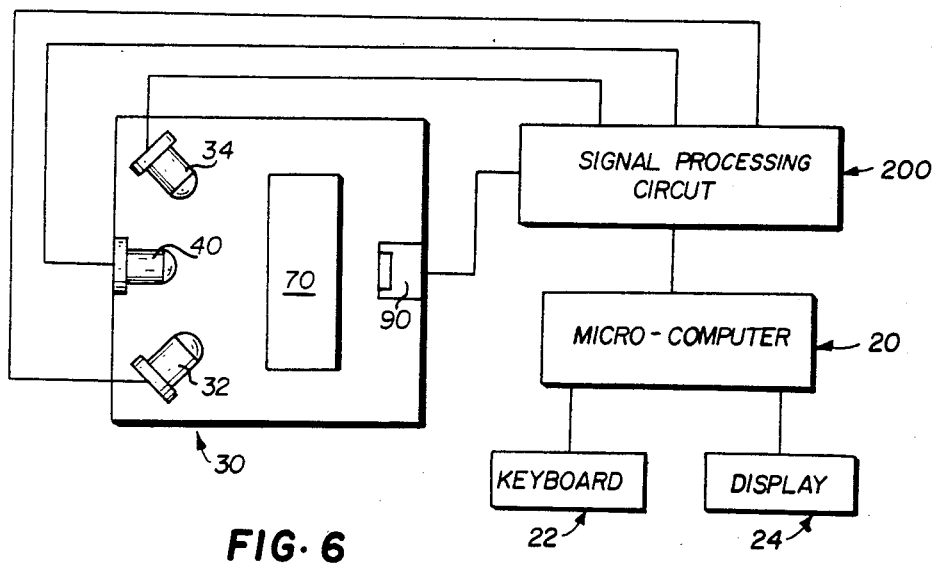
FIG. 6 is a schematic view of the electronic controls of the reflectometer.
Figure 7:
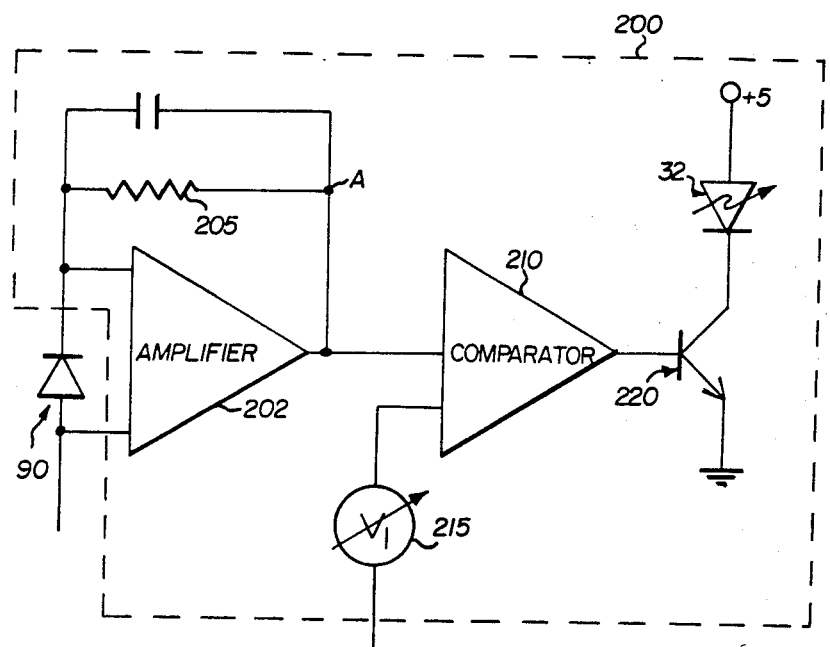
FIG. 7 is a schematic view of the signal processing circuit comprising part of such electronic controls.

To control light sources 32 and 34 by means of detector 90, a signal processing circuit 200 preferably is provided, FIGS. 6 and 7. This circuit receives the signals from both detectors 40 and 90, and controls the voltages applied to light sources 32 and 34. More specifically, circuit 200 comprises, FIG. 6, an amplifier, not shown, for the signal generated by detector 40, and an amplifier 202 for reference detector 90. It also comprises the circuitry which provides the feedback control of each light source. Specifically, it comprises resistor 205 that converts the current generated by reference detector 90 into a voltage at point A. This voltage goes to comparator 210, which compares it with the voltage level $V_1$ of a voltage source 215 preset at the factory. If the voltage at A is less (or greater) than $V_1$, comparator 210 generates a higher (or lower) voltage to transistor 220 to increase (or decrease) the current drive to the light source 32. A switch, not shown, connects the appropriate light source to the signal processing circuit 200 as the user switches from one light source to the other.

Alternatively, circuit 200 is replaced by a ratio circuit not shown, so that the ratio of the light detected by the reference detector during calibration, to the light detected by the reference detector during the test, is applied as a correction factor, as is well-known.

In another embodiment, not shown, light source 32 and detector 40 are reversed in position, so that the illuminating light strikes the supported test element at 90°.

As will be readily apparent, the dimensions x and y of optic portions 30, FIG. 4, which are the horizontal dimensions when in use, are much larger than the third dimension d, FIG. 5. For example, x and y can be about 30 mm and about 34 mm, compared to the 9 mm noted for d above. Because of such dimensions, it is contemplated that the reflectometer containing such optic portions will have a total maximum thickness "t", FIG. 1, between portions 13 and 15 of the exterior surfaces that is no greater than about 1.6 cm, and occupy a total volume no greater than about 1255 cc. Such a thickness and volume make it ideal for carrying in a pocket.

Because planar portion 15 of the bottom wall is generally planar to support surface 37, and is itself adapted to rest on a horizontal surface, support surface 37 of the reflectometer is disposed horizontally when in use. The reflectometer is turned on and properly calibrated. The patient's drop of whole blood is applied to absorbing surface S of element E' already easily placed in the horizontal position shown in FIG. 5. Cover 14 is then closed, and one or more readings are taken. After use, the patient discards element E' and returns the reflectometer to his shirt or coat pocket, a feature rendered possible by the small size of the reflectometer. As a result, the reflectometer readily accompanies the patient so that regular readings can be taken. Because the test element is read horizontally on a large surface area, the patient has no difficulty in placing the test element in its ready position against stop surface 39.

The invention has been described in detail with particular reference to preferred embodiments thereof, but it will be understood that variations and modifications can be effected within the spirit and scope of the invention.

What is claimed is:

1. A compact reflectometer for providing quantitative measurement of reflection densities, said reflectometer comprising
   means for supporting a generally planar test element in a predetermined plane, contacting the reflectometer,
   planar means on a major exterior surface of the reflectometer for orienting said predetermined plane generally horizontally when said planar means is placed on a rest surface,
   a light source constructed to project a beam of light centered on an axis of illumination,
   light detector means constructed to receive light centered on an axis of detection, said light source and said detector means being disposed with said axes each being generally parallel to said planar orienting means of the reflectometer,
   and reflecting means for (a) reflecting light from said source to a predetermined location in said predetermined plane, said source light traveling from said reflecting means along a first path; and (b) reflecting to said detector means only light that is diffusely reflected from a test element at said predetermined location in said predetermined plane, such diffusely reflected light traveling from said reflecting means along a second path; said reflecting means, light source, and detector means being three dimensionally disposed so that said first and second paths do not lie in a common plane.

2. A reflectometer as defined in claim 1, wherein said predetermined plane of the test element is generally parallel to said axes,
   and said directing means comprises at least one reflecting surface for reflecting light to and from a test element supported in said predetermined plane.

3. A reflectometer as defined in claim 1, wherein said first path strikes said predetermined plane at a non-orthogonal angle and said diffusely reflected light extends orthogonally from said predetermined plane.

4. A reflectometer as defined in claim 3, wherein said non-orthogonal angle is about 60°.

5. A reflectometer as defined in claim 1, wherein said reflecting means comprises a single mirror surface disposed to reflect both said source light along said first path and diffusely reflected light along said second path.

6. A reflectometer as defined in claim 1, and further including reference detector means for detecting said light source directly as a reference against which detection by said light detector means is compared, said reflecting means being disposed between said light source and said reference detector means and constructed to pass a fraction of the light received from said light source, to said reference detector means.

7. A reflectometer as defined in claim 1, wherein the total thickness of said reflectometer, is no greater than 2 cm.

8. A reflectometer as defined in claim 1, and further including a light trap disposed to receive light specularly reflected by the supported test element from said light source, and a second light source disposed in said trap with an axis of illumination directed at said reflecting means, said second light source emitting light at a wavelength different from said first-named light source.

* * * * *